United States Patent
Fairway et al.

(10) Patent No.: US 9,242,924 B2
(45) Date of Patent: Jan. 26, 2016

(54) PREPARATION OF A 1-AMINO-3-HYDROXY-CYCLOBUTANE-1-CARBOXYLIC ACID DERIVATIVE

(75) Inventors: Steven Michael Fairway, Oslo (NO); Marit Rolandsgard, Oslo (NO)

(73) Assignee: GE Healthcare Limited, Buckinghamshire (GB)

( * ) Notice: Subject to any disclaimer, the term of this patent is extended or adjusted under 35 U.S.C. 154(b) by 0 days.

(21) Appl. No.: 14/002,184

(22) PCT Filed: Mar. 7, 2012

(86) PCT No.: PCT/EP2012/053867
§ 371 (c)(1),
(2), (4) Date: Aug. 29, 2013

(87) PCT Pub. No.: WO2012/120025
PCT Pub. Date: Sep. 13, 2012

(65) Prior Publication Data
US 2013/0345468 A1  Dec. 26, 2013

Related U.S. Application Data

(60) Provisional application No. 61/450,177, filed on Mar. 8, 2011.

(51) Int. Cl.
*C07C 227/16* (2006.01)
*C07C 269/06* (2006.01)
*A61K 51/04* (2006.01)

(52) U.S. Cl.
CPC .......... *C07C 227/16* (2013.01); *A61K 51/0406* (2013.01); *C07C 269/06* (2013.01); *C07C 2101/04* (2013.01)

(58) Field of Classification Search
None
See application file for complete search history.

(56) References Cited

U.S. PATENT DOCUMENTS

| 8,758,724 B2 | 6/2014 | Ito et al. | |
| 2009/0233903 A1* | 9/2009 | Rodgers et al. | 514/210.21 |

FOREIGN PATENT DOCUMENTS

| EP | 1978015 | 10/2008 |
| WO | 0066579 | 4/2000 |
| WO | 2007/062333 | 5/2007 |
| WO | 2009114512 | 9/2009 |
| WO | 2010047674 | 4/2010 |
| WO | 2011006621 | 1/2011 |

OTHER PUBLICATIONS

Shoup, et.al. Journal of Labelled Compounds and Radiopharmaceuticals, vol. 42, No. 3 Jan. 1, 2999, pp. 215-225.
Yu, et.al. Bioorganic & Medicinal Chemistry, vol. 17, No. 5 Mar. 1, 2009, pp. 1982-1990.
Avram, et.al. Chemische Berichte, vol. 90, 1957, pp. 1424-1431.
Alibes, et.al. Organic Letters, vol. 6, No. 9, 2004, pp. 1449-1452.
PCT/EP2012/053867 ISRWO Dated Jul. 17, 2012.
Baer et al. "Syntheses of L-α-Lecithins Containing Shorter Chain Fatty Acids. Water-soluble Glycerolphosphatides.", J American Chemical Society, 81:2494-2498, (May 20, 1959).

* cited by examiner

*Primary Examiner* — Yevegeny Valenrod
(74) *Attorney, Agent, or Firm* — Parks Woods LLC

(57) ABSTRACT

The invention relates to a process for preparation of radiopharmaceutical precursors, and in particular protected amino acid derivatives which are used as precursors for production of radiolabelled amino acids for use in in vivo imaging procedures such as positron emission tomography (PET). Particularly, the invention relates to a process for preparation of a precursor of the [$^{18}$F]-1-amino-3-fluorocyclobutanecarboxylic acid ([$^{18}$F] FACBC) PET agent, ensuring that the reaction efficiently goes to completion.

7 Claims, No Drawings

PREPARATION OF A 1-AMINO-3-HYDROXY-CYCLOBUTANE-1-CARBOXYLIC ACID DERIVATIVE

This application is a filing under 35 U.S.C. 371 of international application number PCT/EP2012/053867, filed Mar. 7, 2012, which claims priority to U.S. application No. 61/450,177 filed Mar. 8, 2011, the entire disclosure of which is hereby incorporated by reference.

The invention relates to a process for preparation of radiopharmaceutical precursors, and in particular protected amino acid derivatives which are used as precursors for production of radiolabelled amino acids for use in in vivo imaging procedures such as positron emission tomography (PET). Particularly, the invention relates to a process for preparation of a precursor of the [$^{18}$F]-1-amino-3-fluorocyclobutanecarboxylic acid ([$^{18}$F] FACBC) PET agent.

Nuclear medicine examination represented by positron emission tomography (PET) is effective in diagnosing a variety of diseases including heart diseases and cancer. These techniques involve administering an agent labeled with a specific radioisotope (hereinafter referred to as radiopharmaceutical) to a patient, followed by detecting γ-rays emitted directly or indirectly from the agent. Nuclear medicine examination is characteristic in that it has not only high specificity and sensitivity to diseases, but also an advantage of providing information on the functionality of lesions, compared to other examination techniques. For example, [$^{18}$F]2-fluoro-2-deoxy-D-glucose ("[$^{18}$F]FDG"), one radiopharmaceutical used for PET examination, tends to be concentrated in area where glucose metabolism is enhanced, thereby making it possible to specifically detect tumors in which glucose metabolism is enhanced. Nuclear medicine examination is performed by tracing a distribution of an administered radiopharmaceutical, and data obtained there from vary depending on nature of the radiopharmaceutical. Thus, different radiopharmaceuticals have been developed for different diseases, and some of them are put into clinical use. There have been developed, for example, various tumor diagnostic agents, bloodstream diagnostic agents and receptor mapping agents.

In recent years, a series of radioactive halogen-labeled amino acid compounds including [$^{18}$F]-1-amino-3-fluorocyclobutanecarboxylic acid ([$^{18}$F]FACBC) have been designed as novel radiopharmaceuticals. [$^{18}$F]FACBC is considered to be effective as a diagnostic agent for highly proliferative tumors, because it has a property of being taken up specifically by amino acid transporters. Improved processes for preparation of [$^{18}$F]FACBC and its precursors are sought.

EP1978015 (A1) provides processes for producing [$^{18}$F] FACBC on a small scale. One of the intermediates in this process is 1-(N-(t-butoxycarbonyl)amino)-3-hydroxy-cyclobutane-1-carboxylic acid ethyl ester (Formula IV in Scheme 1 below). In the process step of EP1978015 (A1) for preparing this intermediate, dry palladium at neutral pH is used. Scheme 1 shows the multi-step synthesis, as outlined in EP1978015 (A1), for preparation of [$^{18}$F] FACBC.

Scheme 1

Step 1:
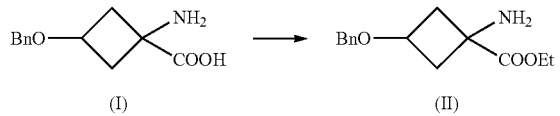

Step 2:

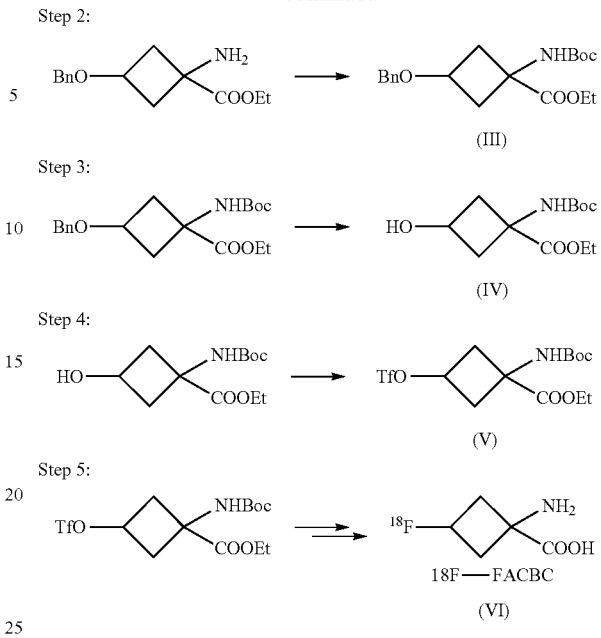

In Scheme 1 above, BnO denotes Benzyl ether, Boc denotes tert-butyl carbamate (tert-butoxycarbonyl) and OTf denotes Trifluoromethanesulfonate.

The last steps of the synthesis of [$^{18}$F]FACBC, performed on an automated synthesiser unit, are based on nucleophilic displacement of a triflate group by [$^{18}$F]fluoride from the precursor of Formula (V). The [$^{18}$F]fluoride may be introduced with a solution of kryptofix (K222), potassium carbonate, water and acetonitrile into the reaction vessel. The $^{18}$F-labelled intermediate compound then undergoes two deprotecting steps, where the ethyl and the Boc protecting groups are removed by basic and acidic hydrolysis, respectively.

The compound of Formula (IV):

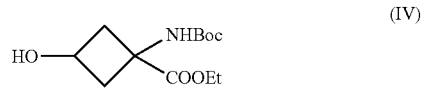 [SMILES: CCOC(=O)C1(NC(=O)OC(C)(C)C)CC(O)C1]

is named 1-(N-(t-butoxycarbonyl)amino)-3-hydroxy-cyclobutane-1-carboxylic acid ethyl ester. This intermediate is prepared by hydrogenolysis of 1-(N-(t-butoxycarbonyl)amino)-3-benzyloxy-cyclobutane-1-carboxylic acid ethyl ester (Formula III), as shown in step 3 of Scheme 1. Such hydrogenolysis, or debenzylation, may be performed by the use of a palladium catalyst and hydrogen gas. In small scale a dry palladium catalyst is acceptable to use, but in a larger scale it would be better to use a wet palladium catalyst from safety perspectives, as palladium is pyrophoric under certain conditions and can hence ignite. However, when performing this hydrogenolysis in larger scale and exchanging the dry palladium with wet palladium, it was experienced that the removal of the benzyl group was incomplete, even after several days. On a smaller scale, and using dry palladium, the hydrogenolysis reaction went to completion after 2-4 days.

Therefore, there is a need for a process for preparing the compound of Formula (IV) which is safe and which efficiently goes to completion.

It has now surprisingly been found that using particular conditions that the process can be successfully carried out using wet palladium. The method of the invention therefore avoids the risks of ignition associated with dry palladium, and the hydrogenolysis reaction goes to completion in an acceptable time period. The solution found is to reduce the pH of the starting material comprising the compound to be hydrogenolysed, and using wet palladium.

Therefore, in a first aspect the invention provides a process for preparation of a compound of Formula IVa:

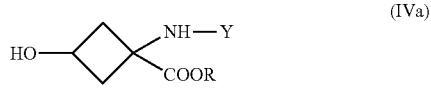

(IVa)

from a compound of Formula IIIa:

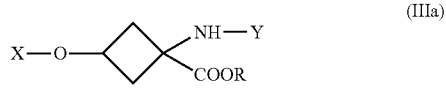

(IIIa)

wherein:
R denotes an alkyl group with 1 to 5 carbon atoms;
Y denotes a protecting group for an amine;
X denotes a protecting group for an alcohol;
wherein the process includes adjusting the pH of a reaction medium comprising the compound of Formula IIIa to 2.0-5.0, and performing a hydrogenolysis of X using a wet catalyst selected from the platinum group metals.

The moiety R is a linear or branched alkyl chain, and is preferably an alkyl group selected from methyl, ethyl, 1-propyl or isopropyl, and is most preferably ethyl.

The term "alkyl", alone or in combination, means a straight-chain or branched-chain alkyl radical having the general formula $C_nH_{2+1}$. Examples of such radicals include methyl, ethyl, and isopropyl.

The term "alcohol" herein refers to a substituent comprising the group —OH.

The term "amine" herein refers to the group —NR'R" wherein R' and R" are independently hydrogen or an alkyl, and are preferably both hydrogen.

By the term "protecting group" is meant a group which inhibits or suppresses undesirable chemical reactions, but which is designed to be sufficiently reactive that it may be cleaved from the functional group in question to obtain the desired product under mild enough conditions that do not modify the rest of the molecule. Protecting groups are well known to those skilled in the art and are described in 'Protective Groups in Organic Synthesis', Theorodora W. Greene and Peter G. M. Wuts, (Fourth Edition, John Wiley & Sons, 2007).

A preferred amino protecting group for use in the present invention is selected from the group consisting of a t-butoxycarbonyl group, an allyloxycarbonyl group, a phthalimide group and N-benzylideneamine substituent. The Y moiety is hence a protecting group for an amine, such as for a carbamate.

The X moiety is a protecting group for alcohol, the protecting group is chosen so that the protecting group forms its related ether, such as; benzyl (Bn), benzyl carbonates, methoxymethyl (MOM), 2-methoxyethoxymethyl (MEM), methylthiomethyl (MTM), tetrahydropyranyl (THP), benzyloxymethyl (BOM), p-Methoxyphenyl, p-methoxybenzyl (MPM), p-methoxybenzyloxymethyl (PMBM), triisopropylsilyl (TIPS), tert-butyldimethylsilyl (TBDMS), 2-(trimethylsilyl)ethoxymethyl (SEM) and (phenyldimethylsilyl)methoxymethyl (SMOM). A group that can be removed by hydrogenation is preferred and in a preferred embodiment X is benzyl.

In a particularly preferred embodiment R is an ethyl group, Y is BOC and X is benzyl such that the compound of Formula IVa is a compound of Formula IV and the compound of Formual IIIa is a compound of Formula III, according to Scheme 1.

The catalyst used in the process of the invention is selected from the group of platinum metal group, and is accordingly selected from the group of ruthenium, rhodium, palladium, osmium, iridium, and platinum. More preferably, the catalyst is palladium.

The catalyst used in the process of the invention should be wet to avoid any risk of ignition. The catalyst used is preferably in the form of a thick slurry, and such slurry includes water. In one embodiment the wet catalyst includes 30-70% weight % water, more preferably 40-60 weight % water, and most preferably 45-55 weight % water. In a particularly preferable embodiment the wet catalyst includes about 50 weight % water. Further, the catalyst used is preferably a heterogeneous catalyst, meaning that it includes solid particles of the metal which is suspended in the reaction medium. The catalyst used in the invention, such as palladium, is preferably distributed over finely divided carbon, referred to as palladium on carbon (Pd/C). Such catalysts are commercially available with a metal loading of 1-30%, and these can be used in the method of the invention. The metal loading, such as the palladium loading, is more preferably 1-10% and most preferably 5-10%. The amount of catalyst to be used in the process depends on which catalyst is chosen, and on the percentage of loading. With e.g. a 10% loaded palladium on carbon catalyst, the amount of catalyst to be used in the method of the invention is 1-30 weight %/compound, more preferably 5-20 weight %/compound and most preferably around 10 weight %/compound. The "compound" in this context is the start material, i.e. a compound of Formula IIIa, such as the compound of Formula III.

The hydrogenolysis reaction of the process of the invention is conducted catalytically using a hydrogen source. The preferred hydrogen source is hydrogen gas.

When performing the process of the invention it has surprisingly been found that by combining the use of wet catalyst and adjusting pH, the debenzylation was successfully driven to completion. The pH of a reaction medium comprising a compound of Formula IIIa, such as a compound of Formula III, and a solvent, is adjusted to 2.0-5.0 by the addition of an acid. More preferably, the pH is adjusted to 2.5-3.5 and most preferably to 3.0. It has surprisingly been found that the debenzylation reaction went to completion at these conditions in an acceptable short time, at the same time as the protecting group of the amine function (group Y) was not affected. This protecting group is later to be removed by acidic hydrolysis, and it is crucial that it is not removed during the dehydrogenolysis step of the process of the invention. The acid used in the process is a mineral acid or an organic acid and is preferably selected from the group of hydrochloric acid, acetic acid, formic acid and sulphuric acid. Most preferably the acid is acetic acid. In the process of the invention the compound of Formula IIIa is hence dissolved in a solvent and the pH is measured and adjusted to the desired level by the addition of an acid to the reaction medium. The solvent used to dissolve the compound of Formula IIIa, such as the compound of Formula III, is a polar solvent, either protic or aprotic, and is preferably selected from the group of alcohols, esters, ethers and chlorinated solvents. The solvent is more preferably an alcohol and most preferably ethanol. The amount of solvent should be sufficient to completely solve the compound of Formula IIIa. The mol/ml ratio between the compound of Formula IIIa and the solvent is e.g. between 1:4 to 1:8.

The process of the invention can be used in all scales and is particularly useful when preparing in large scale, such as when preparing 100 grams or more, such as 300 grams, or up to 500 grams or more, of the compound of Formula IVa. In eral tests were performed to optimize the debenzylation reaction to prepare 1-(N-(t-butoxycarbonyl)amino)-3-hydroxy-cyclobutane-1-carboxylic acid ethyl ester (Compound of Formula IV). Various amounts of acetic acid was added to the reaction media comprising the compound of Formula III and ethanol, to adjust the pH to around 3. Various amounts of palladium on carbon (10% loading), were used for the dehydogenolysis, testing both wet and dry catalysts. The reactions were traced by TLC. The results are found in table 1.

TABLE 1

| Test no. | Compound III (g) | Acetic acid (ml/g compound III) | Pd—C (g/g compound III) | Weight % Pd—C/ compound III (%) | Pd quality | Reaction time (days) | Reaction completion by TLC |
|---|---|---|---|---|---|---|---|
| 1 | 1 | | 0.25 | 25 | dry | 4 | Yes |
| 2 | 20 | | 0.12 | 12 | dry | 2 | Yes |
| 3 | 14 | | 0.12 | 12 | dry | 3 | Almost |
| 4 | 270 | | 0.12 | 12 | dry | 2 | Yes |
| 5 | 30 | | 0.12 | 12 | dry | 8 | No |
| 6 | 3 | | 0.17 | 17 | wet | 8 | No |
| 7 | 3 | | 1.316 | 131.6 | wet | 10 | Yes |
| 8 | 3 | | 0.379 | 37.9 | dry | 5 | Almost |
| 9 | 1 | 0.21 | 0.33 | 16.5 | wet | 2 | Yes |
| 10 | 1 | 0.20 | 0.30 | 15 | wet | 2 | Yes |
| 11 | 1 | 0.20 | 0.10 | 5 | wet | 4 | Yes |
| 12 | 1 | 1.99 | 0.20 | 10 | wet | 2 | Yes |
| 13 | 6 | 0.20 | 0.20 | 10 | wet | 3 | Yes |
| 14 | 32 | 0.25 | 0.20 | 10 | wet | 2 | Yes | smaller scales, a dry platinum group metal catalyst may be used, but when scaling up, for safety reasons it is advantageous to use such catalyst in wet form. The process of the invention including wet palladium and adjusting the pH of the reaction medium to 2.0-5.0 has been found much safer, more efficient, and also more cost efficient as the hydrogenolysis reaction goes to completion in short time. Without the addition of the acid the reaction was incomplete, while when performing the process of the invention the dehydrogenolysis goes to completion, such as in five days or less, preferably in four days or less and most preferably in 3 days of less.

In a further aspect, the invention provides a process for preparing the precursor compound of $^{18}$F-FACBC, according to Formula V:

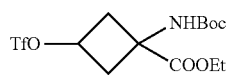

including a step of preparing the compound of Formula IV according to the process of the first aspect. OTf denotes trifluorormethanesulfonate. Y in Formula IVa is then Boc and R is ethyl.

The invention is illustrated by way of the example below.

EXAMPLES

Example 1

1-(N-(t-butoxycarbonyl)amino)-3-benzyloxy-cyclobutane-1-carboxylic acid ethyl ester (Compound of Formula III) in various amounts was added ethanol (18.4-20.0 ml/g). Sev- It was found that when using the palladium catalyst in the wet form, and adjusting the pH to around 3, the reaction went to completion in only 2-4 days. Without the pH adjustment, performing the reaction at neutral pH, and using wet palladium, the debenzylation did either not go to completion, or it took as much as 10 days to complete.

The invention claimed is:

1. A process for preparation of a [18F]-FACBC precursor compound of Formula IVa:

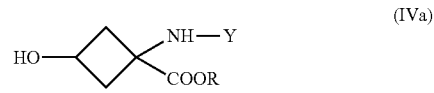

from a compound of Formula IIIa:

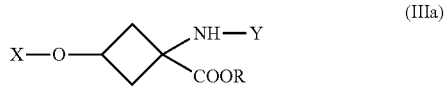

wherein:
R denotes an alkyl group with 1 to 5 carbon atoms; Y denotes a protecting group for an amine; and,
X denotes a protecting group for an alcohol;
wherein the process is used to prepare at least 100 gram batch sizes of Formula IVa and goes to completion based on TLC in five or less days, and includes using an acid to adjust the pH of a reaction medium comprising the compound of Formula IIIa and ethanol to 2.0-5.0, adjusting the amounts of Formula IIIa and ethanol, and performing a hydrogenolysis of X using a wet palladium on carbon catalyst.

2. A process as defined in claim 1 wherein R is an ethyl group, Y is BOC and X is benzyl.

3. A process as defined in claim 1 wherein said catalyst has a palladium loading of 1-10%.

4. A process as defined in claim 1 wherein the acid is acetic acid.

5. A process as defined in claim 1 wherein the pH is adjusted to 2.5-3.5.

6. A process as defined in claim 1 wherein said catalyst is in the form of a slurry comprising 30% to 70% water by weight.

7. A process as defined in claim 6 wherein said slurry comprises about 50% water by weight.

\* \* \* \* \*